United States Patent [19]

Ueno

[11] Patent Number: 5,405,846
[45] Date of Patent: Apr. 11, 1995

[54] TREATMENT OF OCULAR HYPERTENSION WITH A SYNERGISTIC COMBINATION

[75] Inventor: Ryuji Ueno, Nishinomiya, Japan

[73] Assignee: R-Tech Ueno, Ltd., Osaka, Japan

[21] Appl. No.: 127,368

[22] Filed: Sep. 28, 1993

[30] Foreign Application Priority Data

Oct. 1, 1992 [JP] Japan .................................. 4-284956

[51] Int. Cl.⁶ .................. A61K 31/535; A61K 31/19; A61K 31/215
[52] U.S. Cl. .................. 514/235.8; 514/530; 514/573; 514/913
[58] Field of Search ............. 514/530, 573, 913, 235.8

[56] References Cited

U.S. PATENT DOCUMENTS 4,952,581  8/1990  Bito et al. .................. 514/236.2

FOREIGN PATENT DOCUMENTS 0286903  10/1988  European Pat. Off. .
0471856   3/1991  European Pat. Off. .
0458590   5/1991  European Pat. Off. .
93307748  5/1991  European Pat. Off. .
0561073   9/1993  European Pat. Off. .
63-313728 12/1988 Japan .

*Primary Examiner*—Zohreh Fay

[57] ABSTRACT

A method for treatment of ocular hypertension which comprises ocularly administering, to a subject in need of such treatment, an ocular-hypertension synergistic combination of
  (a) a 15-deoxy-prostaglandin compound, and
  (b) a β-adrenergic blocker in an amount effective in treatment of ocular hypertension.

1 Claim, No Drawings

TREATMENT OF OCULAR HYPERTENSION WITH A SYNERGISTIC COMBINATION

The present invention relates to a treatment of ocular hypertension with a synergistic combination comprising (a) a 15-deoxy-prostaglandin compound and (b) a β-adrenergic blocker.

The compounds used as the component (a) in the present invention are prostaglandin analogues which can be obtained synthetically.

Prostaglandins (hereinafter, prostaglandins are referred to as PGs) are members of a class of organic carboxylic acid that are contained in human and most other mammalian tissues or organs and that exhibit a wide range of physiological activities. Naturally occurring PGs Dossess as a common structural feature the prostanoic acid skeleton:

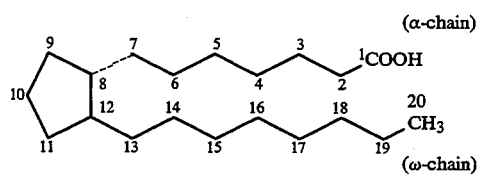

Some synthetic analogues have somewhat modified skeletons. The primary PGs are classified based on the structural feature of the five-membered cycle moiety into PGAs, PGBs, PGCs, PGDs, PGEs, PGFs, PGGs, PGHs, PGIs and PGJs, and also on the presence or absence of unsaturation and oxidation in the chain moiety as:

Subscript 1—13,14-unsaturated-15—OH
Subscript 2—5,6- and 13,14-diunsaturated-15—OH
Subscript 3—5,6- and 13,14- and 17,18-tri-unsaturated-15—OH Further, PGFs are sub-classified according to the configuration of hydroxy group at position 9 into α(hydroxy group being in the alpha configuration) and β(hydroxy group being in the bata configuration).

The fact that the above compounds under item (a) have ocular hypotensive activity has been known by WO 91/13869. It has also been described in Japanese Patent Publication No. A-313728/1988, page 7, column 3, line 7 from bottom to page 8, column 4, line 4, that a combination of $PGF_2\alpha$ isopropyl ester and Timolol (an agent for treating glaucoma) may be advantageous because the ocular hypotensive activity of the former is not inhibited by a β-adrenergic blocker such as the latter. Such description, however, neither show a combined use of the β-adrenergic blocker and the component (a) in the present invention nor suggest that said combined use may synergistic increase in effect or decrease in side-effect because $PGF_2\alpha$ is a primary PG having a trans double bond between positions 13 and 14, a hydroxy group (in α-conformation) at position 15 and 20 carbon atoms in the basic structure, while the 15-deoxy-PGs are compounds having no hydroxy group at 15-position which has been considered as an important group for activities of primary PGs and thus significantly different from the primary $PGF_2\alpha$.

After an extensive study on the possibility that the effect of the component (a) in the present invention is improved by combining it with a variety of compounds, the present inventor has surprisingly discovered that the effect of the component (a) is significantly improved and side-effect is decreased by coadministration with a β-adrenergic blocker such as Timolol. Said discovery leads to the present invention.

In a first aspect, the present invention provides a method for treatment of ocular hypertension which comprises ocularly administering, to a subject in need of such treatment, an oculo-hypotensively synergistic combination of (a) a 15-deoxy-prostaglandin compound, and
(b) a β-adrenergic blocker in an amount effective in treatment of ocular hypertension.

In a second aspect, the present invention provides a use of an oculo-hypotensively synergistic combination of (a) a 15-deoxy-prostaglandin compound, and
(b) a β-adrenergic blocker for the manufacture of a medicament useful in treatment of ocular hypertension.

In a third aspect, the present invention provides a pharmaceutical composition for treatment of ocular hypertension which comprising an oculo-hypotensively synergistic combination of (a) a 15-deoxy-prostaglandin compound, and
(b) a β-adrenergic blocker in association with a pharmaceutically acceptable carrier, diluent or excipient.

The "15-deoxy-prostaglandin compounds", used as the component (a) in the present invention and referred to as the component (a), include any prostaglandin derivatives which have no hydroxy group at position 15 of the prostanoic acid nucleus.

Nomenclature of the component (a) herein uses the numbering system of prostanoic acid represented in formula (A) shown above.

While formula (A) shows a basic skeleton having twenty carbon atoms, the 15-deoxy-PG compounds used in the present invention are not limited to those having the same number of carbon atoms. The carbon atoms in Formula (A) are numbered 2 to 7 on the α-chain starting from the α-carbon atom adjacent to the carboxylic carbon atom which is numbered 1 and towards the five-membered ring, 8 to 12 on the said ring starting from the carbon atom on which the α-chain is attached, and 13 to 20 on the ω-chain starting from the carbon atom adjacent to the ring. When the number of carbon atoms is decreased in the α-chain, the number is deleted in order starting from position 2 and when the number of carbon atoms is increased in the α-chain, compounds are named as substituted derivatives having respective substituents at position 1 in place of carboxy group (C-1). Similarly, when the number of carbon atoms is decreased in the ω-chain, the number is deleted in order starting from position 20 and when the number of carbon atoms is increased in the ω-chain, compounds are named as substituted derivatives having respective substituents at position 20. Stereochemistry of the compounds is the same as that of above formula (A) unless otherwise specified. Thus, 15-deoxy-PG compounds having 10 carbon atoms in the ω-chain is nominated as 15-deoxy-20-ethyl-PGs.

The above formula expresses a specific configuration which is the most typical one, and in this specification compounds having such a configuration are expressed without any specific reference to it.

In general PGDs, PGEs and PGFs have a hydroxy group on the carbon atom at positions 9 and/or 11 but in the present specification the term "15-deoxy-PG compounds" includes PGs having a group other than a hydroxyl group at positions 9 and/or 11. Such PGs are referred to as 9-dehydroxy-9-substituted-PG compounds or 11-dehydrox-y-11-substituted-PG compounds.

Examples of substitution products or derivatives include pharmaceutically or physiologically acceptable salts and esters at the carboxy group at the alpha chain, unsaturated derivatives having a double bond or a triple bond between positions 2 and 3 or positions 5 and 6, respectively, substituted derivatives having substituent(s) on carbon atom(s) at positions 3, 5, 6, 16, 17, 19 and/or 20 and compounds having lower alkyl or a hydroxy (lower) alkyl group at positions 9 and/or 11 in place of the hydroxy group, of the above PGs.

Examples of substituents present in preferred compounds are as follows: Substituents on the carbon atom at positions 3, 17 and/or 19 include lower alkyl, for example, $C_{1-4}$ alkyl, especially methyl and ethyl. Substituents on the carbon atom at position 16 include lower alkyl, e.g., methyl, ethyl, etc., hydroxy and halogen atom, e.g., chlorine, fluorine, etc., aryl, e.g., phenyl, aryloxy, e.g., phenoxy, etc. Substituents on the carbon atom at position 17 include halogen atom, e.g., chlorine, fluorine, etc., aryl, e.g., phenyl, aryloxy, e.g., phenoxy, etc. Substituents on the carbon atom at position 20 include saturated and unsaturated lower alkyl, e.g., $C_{1-6}$ alkyl, lower alkoxy, e.g., $C_{1-4}$ alkoxy and lower alkoxy (lower) alkyl, e.g., $C_{1-4}$ alkoxy-$C_{1-4}$ alkyl. Substituents on the carbon atom at position 5 include halogen atom, e.g., chlorine, fluorine, etc. Substituents on the carbon atom at position 6 include oxo group forming carbonyl. Stereochemistry of PGs having hydroxy, lower alkyl or lower (hydroxy) alkyl substituent on the carbon atom at positions 9 and/or 11 may be alpha, beta or mixtures thereof.

A group of preferred compounds used in the present invention has the formula

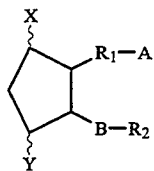

(I)

wherein X and Y are hydrogen, hydroxy, halo, lower alkyl, hydroxy(lower)alkyl, or oxo, with the proviso that at least one of X and Y is a group other than hydrogen, and 5-membered ring may have at least one double bond, A is —COOH or its pharmaceutically acceptable salt or ester, B is —CH$_2$—CH$_2$—CH$_2$—, —CH=CH—CH$_2$—, —CH$_2$—CH=CH—, —C≡C—CH$_2$— or —CH$_2$—C≡C—, R$_1$ is bivalent saturated or unsaturated, lower or medium aliphatic hydrocarbon residue which is unsubstituted or substituted with halo, oxo or aryl, R$_2$ is saturated or unsaturated, lower or medium aliphatic hydrocarbon residue, which is unsubstituted or substituted with halo, lower alkoxy, lower alkanoyloxy, cyclo(lower)alkyl, aryl or aryloxy.

In the above formula, the term "unsaturated" in the definitions for R$_1$ and R$_2$ is intended to include at least one and optionally more than one double bond and/or triple bond isolatedly, separately or serially present between carbon atoms of the main and/or side chains. According to usual nomenclature, an unsaturation between two serial positions is represented by denoting the lower number of said two positions, and an unsaturation between two distal positions is represented by denoting both of the positions. Preferred unsaturation is a double bond at position 2 and a double or triple bond at position 5.

The term "lower or medium aliphatic hydrocarbon residue" refers to a straight or branched chain hydrocarbyl group having 1 to 14 carbon atoms, respectively, (for a side chain, 1 to 3 carbon atoms being preferred) and preferably 2 to 8 carbon atoms for R$_1$ and 1 to 9 carbon atoms for R$_2$.

The term "halo" denotes fluoro, chloro, bromo and iodo.

The term "lower" throughout the specification is intended to include a group having 1 to 6 carbon atoms unless otherwise specified.

The term "lower alkyl" includes saturated and straight or branched chain hydrocarbon radicals containing 1 to 6, carbon atoms, e.g., methyl, ethyl, propyl, isopropyl, butyl, isobutyl, t-butyl, pentyl and hexyl.

The term "lower alkoxy" refers to the group lower-alkyl-O- wherein lower alkyl is as defined above.

The term "hydroxy(lower)alkyl" refers to lower alkyl as defined above which is substituted with at least one hydroxyl group, e.g., hydroxymethyl, 1-hydroxyethyl, 2-hydroxyethyl and 1-methyl-1-hydroxyethyl.

The term "lower alkanoyloxy" refers to a group of the formula: RCO—O— wherein RCO— is an acyl group formed by oxidation of a lower alkyl group as defined above, e.g., acetyl.

The term "cyclo(lower)alkyl" refers to a cyclic group formed by cyclization of a lower alkyl group as defined above.

The term "aryl" includes unsubstituted or substituted aromatic carbocyclic or heterocyclic (preferably monocyclic) groups, e.g., phenyl, tolyl, xylyl and thienyl. Examples of substituents are halo and halo(lower)alkyl wherein halo and lower alkyl being as defined above.

The term "aryloxy" refers to a group of the formula: ArO- wherein Ar is aryl as defined above.

Suitable "pharmaceutically acceptable salts" includes conventional non-toxic salts, and may be a salt with an inorganic base, for example an alkali metal salt (e.g., sodium salt, potassium salt, etc.) and an alkaline earth metal salt (e.g., calcium salt, magnesium salt, etc.), ammonium salt, a salt with an organic base, for example, an amine salt (e.g., methylamine salt, dimethylamine salt, cyclohexylamine salt, benzylamine salt, piperidine salt, ethylenediamine salt, ethanolamine salt, diethanolamine salt, triethanolamine salt, tris(hydroxymethanlamino)ethane salt, monomethyl-monoethanolamine salt, procaine salt, caffeine salt, etc.), a basic amino acid salt (e.g., arginine salt, lysine salt, etc.), tetraalkyl ammonium salt and the like. These salts can be prepared by the conventional process, for example from the corresponding acid and base or by salt interchange.

Examples of the "pharmaceutically acceptable esters" are aliphatic esters, for example, lower alkyl ester, e.g., methyl ester, ethyl ester, propyl ester, isopropyl ester, butyl ester, isobutyl ester, t-butyl ester, pentyl ester, 1-cyclopropylethyl ester, etc., lower alkenyl ester e.g., vinyl ester, allyl ester, etc., lower alkynyl ester e.g, ethynyl ester, propynyl ester, etc., hydroxy(lower)alkyl ester, e.g., hydroxyethyl ester, lower alkoxy(lower)alkyl ester, e.g., methoxymethyl ester, 1-methoxyethyl ester, etc., and aromatic esters, for example, optionally substituted aryl ester, e.g., phenyl ester, tosyl ester, t-butylphenyl ester, salicyl ester, 3,4-di-methoxyphenyl ester, benzamidophenyl ester, etc., aryl(lower)alkyl ester, e.g., benzyl ester, trityl ester, benzhydryl ester, etc.

The term "pharmaceutically" is intended to be "ophthalmically" when used in connection with an ophthalmic composition.

Preferred examples of A include —COOH, —COOCH$_3$, —COOCH$_2$CH$_3$ and —COOCH(CH$_3$)$_2$.

The configuration of the ring and the α- and/or ω-chain in the above formula (I) may be the same as or different from that in the primary PGs. However, the present invention also includes a mixture of a compound having a primary configuration and that of an unprimary configuration.

Examples of the typical compounds of the present invention are 15-deoxy-PGAs to Fs and their derivatives, e.g., 20-loweralkyl-derivatives, Δ$^2$-derivatives, 3R,S-methyl-derivatives, 6-oxo-derivatives, 5R,S-fluoroderivatives, 5,5-difluoro-derivatives, 16R,S-methyl-derivatives, 16,16-dimethyl-derivatives, 16R,S-fluoro-derivatives, 16,16-difluoro-derivatives, 17S-methyl-derivatives, 17R,S-fluoro-derivatives, 17,17-difluoro-derivatives, 17-phenyl-derivatives, 17-phenoxy-derivatives and 19-methyl-derivatives.

In the present invention, any of the individual tautomeric isomers, a mixture thereof, or optical isomers, a mixture thereof, a racemic mixture, and other isomers such as steric isomers can be used in the same purpose.

Some of the compounds used in the present invention may be prepared by the method disclosed in WO 91/13869.

Alternatively, these compounds may be prepared by a process analogous to that described in the above publications in combination with the known synthetic method for the five-membered ring moiety.

The β-adrenergic blockers used as the component (b) in the present invention refer to agents capable of blocking the β-adrenergic receptor. Typical examples of such agents are relatively less selective β-adrenergic receptor blocking agents which are represented by the following formula:

A—OCH$_2$CH(OH)CH$_2$NHC(CH$_3$)(R)

wherein A is an aromatic group and R is hydrogen atom or methyl.

The above group A includes 4-morpholine-1,2,5-thiadiazol-3-yl, 2-acetylbenzofuran-7-yl, 1,2,3,4-tetrahydro-2-oxo-quinoline-5-yl. Preferred include Timolol, Befunolol, Betaxolol, Levabunolol, Carteolol and pharmaceutically acceptable salts thereof such as inorganic salts, e.g., hydrochloride or organic salts, e.g., maleate.

Since the component (a) has an activity of lowering ocular pressure without accompanying transient ocular hypertension as shown by the primary PGs, the combination of (a) and (b) can be used for the treatment of various disease and conditions in which lowering of ocular pressure is desirous, for example glaucoma, ocular hypertension and other disease which accompanies increase in ocular pressure.

As used herein, the term "treatment" or "treating" refers to any means of control of a disease in a mammal, including preventing the disease, curing the disease, relieving the disease and arresting or relieving the development of the disease.

The combination has an advantage, by containing the component (b) in addition to the component (a), that it has a synergistically increased ocular hypotensive action, thus enabling reduce in dosage, and/or lowering the side-effect.

The ratio (a):(b) in the combination varies, without limitation, ordinarily within the range 1:0.5 to 1:200, preferably 1:1 to 1:100 and most preferably 1:2 to 1:50.

While the dosage of the component (a) varies depending on condition of the component (a) varies depending on condition of the patient, severity of the disease, purpose of the treatment, judgment of the physician and total dosage of the combination, it is ordinarily within the range 0.005 to 2% and preferably 0.01 to 1% by weight.

The dosage of the component (b) varies, for example, depending on the concentration of the component (a) and ordinarily within the range 0.005 to 20% and preferably 0.01 to 10% by weight.

The combination according to the present invention can be administered in the form of a pharmaceutical composition containing the component (a) and (b) and optionally other ingredients conveniently used in the ophthalmic composition, such as carrier, diluent or excipient.

The ophthalmic composition used according to the invention includes liquids such as ophthalmic solution, emulsion, dispersion, etc. and semisolids such as ophthalmic gel, ointment, etc. Diluents for the aqueous solution or suspension includes, for example, distilled water and physiological saline. Diluents for the nonaqueous solution and suspension include, for example, vegetable oils, e.g., olive oil, liquid paraggine, mineral oil, and propylene glycol and p-octyldodecanol. The composition may also contain isotonization agents such as sodium chloride, boric acid, sodium citrate, etc. to make isotonic with the lacrimal fluid and buffering agents such as borate buffer, phosphate buffer, etc. to maintain pH about 5.0 to 8.0. Further, stabilizers such as sodium sulfite, propylene glycol, etc., chelating agents such as sodium edetate, etc., thickeners such as glycerol, carboxymethylcellulose, carboxyvinyl polymer, etc. and preservatives such as methyl paraben, propyl paraben, etc. may also be added. These can be sterilized, e.g., by passing through a bacterial filter or by heating.

The ophthalmic ointment may contain vaseline, Plastibase, Macrogol, etc. as a base and surfactant for increasing hydrophilicity. It may also contain geling agents such as carboxymethylcellulose, methylcellulose, carboxyvinyl polymer, etc.

In addition, the composition may contain antibiotics such as chloramphenicol, penicilin, etc. in order to prevent or treat bacterial infection.

The present invention provides a method for treatment of ocular hypertension or glaucoma which comprises ocularly administering the combination of this invention to a subject in need of such treatment, in an amount effective in treatment of ocular hypertension.

Further, the present invention provides a method for treatment of ocular hypertension or glaucoma which comprises ocularly administering simultaneously or seqentially to a subject in need of such treatment, separately the component (a) and the component (b) in an amount effective in treatment of ocular hypertension.

And it enables to get more superior synergistic effect to administer the component (b) with periodically administering of the component (a).

A more complete understanding of the present invention can be obtained by reference to the following Examples which are provided herein for purpose of illustration only and are not intended to limit the scope of the invention.

Test Example 1

Cynomolgus monkeys (male, weight: 6.1–7.4 kg, 3 animals/group) were fixed and intramuscularly anesthetized by 5.0–7.5 mg/kg of Ketamine. The ocular pressure measured at 0.5–1 hour after the fixation was taken as the 0 hour value and values of pressure thereafter were measured in the course of time administering by eye-dropping each 35μl of the following formulations. An electronic pneumatonometer (Alcon) was used for measurement. Decrease in ocular pressure (mean value) at 5 hours after administration of each of the formulations was compared in the Table 1.

| Formulation Example 1 (Comparative) | |
|---|---|
| Timolol maleate | 0.1 g |
| Sterilized water | g.s. to 100 ml |
| Formulation Example 2 (Comparative) | |
| 15-deoxy-PGF$_2$ α Sodium salt, hereinafter referred to as Compound A | 0.01 g |
| Sterilized water | g.s. to 100 ml |
| Formulation Example 3 | |
| Timolol maleate | 0.1 g |
| Compound A | 0.01 g |
| Sterilized water | g.s. to 100 ml |

TABLE 1

| | Decrease in ocular pressure (mmHg) |
|---|---|
| Formulation 1 | −0.3 |
| Formulation 2 | −0.1 |
| Formulation 3 | −2.8 |

The above results show that the combined use of Timolol maleate and Compound A result in a synergistic effect.

What we claim is:

1. A method for treatment of ocular hypertension which comprises ocularly administering, to a subject in need of such treatment, an ocular-hypotension synergistic combination of
   (a) a 15-deoxy-prostaglandin F$_{2\alpha}$, or a pharmaceutically acceptable salt thereof, or pharmaceutically acceptable ester thereof, and
   (b) Timolol, or a pharmaceutically acceptable salt thereof in an amount effective in treatment of ocular hypertension.

* * * * *